(12) United States Patent
Pahlevan et al.

(10) Patent No.: US 9,480,406 B2
(45) Date of Patent: *Nov. 1, 2016

(54) INTRINSIC FREQUENCY ANALYSIS FOR LEFT VENTRICLE EJECTION FRACTION OR STROKE VOLUME DETERMINATION

(71) Applicant: CALIFORNIA INSTITUTE OF TECHNOLOGY, Pasadena, CA (US)

(72) Inventors: Niema Pahlevan, Pasadena, CA (US); Peyman Tavallali, Pasadena, CA (US); Derek Rinderknecht, Arcadia, CA (US); Morteza Gharib, Altadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/517,702

(22) Filed: Oct. 17, 2014

(65) Prior Publication Data

US 2015/0112219 A1 Apr. 23, 2015

Related U.S. Application Data

(60) Provisional application No. 62/003,735, filed on May 28, 2014, provisional application No. 61/893,063, filed on Oct. 18, 2013.

(51) Int. Cl.
| | | |
|---|---|---|
| *A61B 5/05* | (2006.01) | |
| *A61B 5/024* | (2006.01) | |
| *A61B 8/02* | (2006.01) | |
| *A61B 8/08* | (2006.01) | |
| *A61B 5/029* | (2006.01) | |
| *A61B 5/00* | (2006.01) | |

(Continued)

(52) U.S. Cl.
CPC ............. *A61B 5/029* (2013.01); *A61B 5/0004* (2013.01); *A61B 5/02028* (2013.01); *A61B 5/02405* (2013.01); *A61B 5/7235* (2013.01); *A61B 5/7282* (2013.01); *A61B 8/065* (2013.01)

(58) Field of Classification Search
None
See application file for complete search history.

(56) References Cited

U.S. PATENT DOCUMENTS

| | | |
|---|---|---|
| 4,933,545 A | 6/1990 | Saaski et al. |
| 4,991,197 A | 2/1991 | Morris |
| 5,086,776 A | 2/1992 | Fowler, Jr. et al. |

(Continued)

FOREIGN PATENT DOCUMENTS

| | | |
|---|---|---|
| EP | 1279370 A1 | 1/2003 |
| JP | 2002-065677 | 3/2002 |

(Continued)

OTHER PUBLICATIONS

WO, PCT/US2012/069947 ISR, Feb. 27, 2013.

(Continued)

*Primary Examiner* — Carl H Layno
*Assistant Examiner* — Jon Eric C Morales
(74) *Attorney, Agent, or Firm* — One LLP

(57) ABSTRACT

Hardware and software methodology are described for non-invasively monitoring cardiac health. Hemodynamic waveforms variously acquired for a subject are analyzed to calculate or approximate intrinsic frequencies in two domains in two domains across the Dicrotic Notch. Together with associated notch timing, heart rate and blood pressure values left ventricle ejection fraction and/or stroke volume can be determination.

11 Claims, 4 Drawing Sheets

(51) Int. Cl.
A61B 8/06 (2006.01)
A61B 5/02 (2006.01)

(56) References Cited

U.S. PATENT DOCUMENTS

| | | | |
|---|---|---|---|
| 5,146,083 | A | 9/1992 | Zuckerwar et al. |
| 5,265,615 | A | 11/1993 | Frank et al. |
| 5,309,916 | A | 5/1994 | Hatschek |
| 6,135,957 | A | 10/2000 | Cohen-Bacrie et al. |
| 6,477,406 | B1 | 11/2002 | Turcott |
| 6,483,929 | B1 | 11/2002 | Murakami et al. |
| 6,491,647 | B1 | 12/2002 | Bridger et al. |
| 6,676,608 | B1 | 1/2004 | Keren |
| 6,738,734 | B1 | 5/2004 | Huang |
| 7,272,431 | B2 | 9/2007 | McGrath |
| 7,811,234 | B2 | 10/2010 | McGrath |
| 7,889,053 | B2 | 2/2011 | McGrath et al. |
| 8,033,996 | B2 | 10/2011 | Behar |
| 8,232,866 | B2 | 7/2012 | McGrath et al. |
| 8,435,181 | B2 | 5/2013 | Yang et al. |
| 9,026,193 | B2 | 5/2015 | Pahlevan et al. |
| 2003/0069508 | A1 | 4/2003 | Kawaguchi et al. |
| 2003/0135124 | A1 | 7/2003 | Russell |
| 2003/0191400 | A1 | 10/2003 | Shalman et al. |
| 2004/0088123 | A1 | 5/2004 | Ji |
| 2005/0143667 | A1 | 6/2005 | Park et al. |
| 2007/0016031 | A1 | 1/2007 | Mourad et al. |
| 2007/0185391 | A1 | 8/2007 | Morgan |
| 2007/0210786 | A1 | 9/2007 | Allen et al. |
| 2007/0238995 | A1 | 10/2007 | Sui et al. |
| 2008/0234568 | A1 | 9/2008 | Ouchi |
| 2009/0018422 | A1 | 1/2009 | Banet et al. |
| 2009/0204012 | A1 | 8/2009 | Joeken |
| 2010/0185084 | A1 | 7/2010 | Zhang |
| 2011/0040181 | A1 | 2/2011 | Yokota et al. |
| 2011/0130800 | A1 | 6/2011 | Weinstein et al. |
| 2011/0224529 | A1 | 9/2011 | Lading |
| 2011/0275936 | A1 | 11/2011 | Cho et al. |
| 2012/0143068 | A1 | 6/2012 | Cheng et al. |
| 2012/0146796 | A1 | 6/2012 | Margon et al. |
| 2012/0238834 | A1 | 9/2012 | Hornick |
| 2012/0289848 | A1 | 11/2012 | Li et al. |
| 2013/0078095 | A1 | 3/2013 | Olesen |
| 2013/0172723 | A1 | 7/2013 | Baxi et al. |
| 2013/0184573 | A1 | 7/2013 | Pahlevan et al. |
| 2014/0073969 | A1 | 3/2014 | Zou et al. |

FOREIGN PATENT DOCUMENTS

| | | |
|---|---|---|
| KR | 10-2002-0055362 | 7/2002 |
| KR | 10-2003-0070315 | 8/2003 |
| KR | 10-2006-0004931 | 1/2006 |
| WO | WO 2012/011029 | 1/2012 |

OTHER PUBLICATIONS

WO, PCT/US2012/071452 ISR, Mar. 14, 2013.
WO, PCT/US2013/053068 ISR, Nov. 26, 2013.
WO, PCT/US2013/054529 ISR, Nov. 27, 2013.
WO, PCT/US2012/069947 IPRP, Jun. 17, 2014.
WO PCT/US2012/071452 IPRP, Jun. 24, 2014.
Abbas, A. E., et al., "Echocardiographic Determination of Mean Pulmonary Artery Pressure", The American Journal of Cardiology, 2003, vol. 92, pp. 1373-1376.
Angtuaco, M. J., et al., "Noninvasive Estimation of Diastolic Pulmonary Artery Pressure by Doppler Analysis of Tricuspid Regurgitation Velocity in Pediatric Patients", Congent. Heart Dis., 2011, pp. 1-8.
Cremer, A., et al., "Determination of central blood pressure by a noninvasive method (brachial BP and QKD interval)", J. Hypertens., 2012, vol. 30, pp. 1-7.
Daubechies, I., "The Wavelet Transform, Time-Frequency Localization and Signal Analysis", IEEE Transactions on Information Theory, 1990, vol. 36, No. 5, pp. 961-1005.
Denardo, S.J., et al., "Pulse Wave Analysis of the Aortic Pressure Waveform in Severe Left Ventricular Systolic Dysfunction", Circ Heart Fan, 2010, vol. 3, pp. 149-156.
Feng, J., et al., "Determination of wave speed and wave separation in the arteries using diameter and velocity", Journal of Biomechanics, 2010, vol. 43, pp. 455-462.
Fletcher, R. R., et al., "Clip-on wireless wearable microwave sensor for ambulatory cardiac monitoring", IEEE, 2010, pp. 365-369.
Friedberg, M. K., et al., "A Novel Echocardiographic Doppler Method for Estimation of Pulmonary Arterial Pressures", J. Am. Soc. Echocard., 2006, pp. 559-562.
Greenfiled, Jr., J. C., et al., "Relation between pressure and diameter in main pulmonary artery of man", J. Appl. Physiol., 1963, vol. 18, No. 3, pp. 557-559.
Hou, T.Y. et al., "Adaptive Data Analysis via Sparse Time-Frequency Representation", Advances in Adaptive Data Analysis, 2011, vol. 3, Nos. 1 & 2, pp. 1-28.
Hou, T.Y. et al., "Data-driven time-frequency analysis", Appl. Comput, Harman. Anal., 2013, vol. 35, pp. 284-308.
Huang, N.E., et al., "The empirical mode decomposition and the Hilbert spectrum for nonlinear and non-stationary time series analysis", Proc. R. Soc. Lond. A, 1998, vol. 454, pp. 903-995.
Huang, W., et al., "Use of intrinsic modes in biology: Examples of indicial response of pulmonary blood pressure to ± step hypoxia", Proc. Natl. Acad. Sci. USA, 1998, vol. 95, pp. 12766-12771.
Lanzarini, L., et al., "Noninvasive estimation of both systolic and diastolic pulmonary artery pressure from Doppler analysis of tricuspid regurgitant velocity spectrum in patients with chronic heart failure", American Heart Journal, 2002, vol. 144, pp. 1087-1094.
Lee, J. Y., et al., "A Microprocessor-Based Noninvasive Arterial Pulse Wave Analyzer", IEEE Transactions on Biomedical Engineering, 1985, vol. BME-32, No. 6, pp. 451-455.
Milan, A., et al., "Echocardiographic Indexes for the Non-Invasive Evaluation of Pulmonary Hemodynamics", J. Am. Soc. Echocard., 2010, vol. 23, No. 3, pp. 225-239.
Pahlevan, N.M., et al., "A Physiologically Relevant, Simple Outflow Boundary Model for Truncated Vasculature", Annals of Biomedical Engineering, 2011, vol. 39, No. 5, pp. 1470-1481.
Pahlevan, N.M., et al., "Low pulse pressure with high pulsatile external left ventricular power: Influence of aortic waves", Journal of Biomechanics, 2011, vol. 44, No. 11, pp. 2083-2089.
Pahlevan, N.M., et al., "Aortic Wave Dynamics and Its Influence on Left Ventricular Workload", PLoS One, 2011, vol. 6, No. 8, pp. 1-8.
Pahlevan, N.M., et al., "A Bio-Inspired Approach for the Reduction of Left Ventricular Workload", PLoS One, 2014, vol. 9, No. 1, pp. 1-12.
Pahlevan, N.M., et al., "Intrinsic frequency for a systems approach to haemodynamic waveform analysis with clinical applications", Journal of the Royal Society Interface, 2014, vol. 11, pp. 1-10.
Patel, D. J., et al., "Mechanical properties and dimensions of the major pulmonary arteries", J. Appl. Physiol., 1960, vol. 15, No. 1, pp. 92-96.
Selton-Suty, C., et al., "Non-invasive investigations of the right heart: How and why?", Archives of Cardiovascular Disease, 2009, vol. 102, pp. 219-232.
Singh, A., et al., "Pulse Pressure Monitoring Through Non-Contact Cardiac Motion Detection Using 2.45 GHz Microwave Doppler Radar", Engineering in Medicine and Biology Society, 33rd Annual International Conference of the IEEE EMBS, Boston, Massachusetts, USA, Aug. 30-Sep. 3, 2011.
WO, PCT/US2013/053068 IPRP, Feb. 3, 2015.
WO, PCT/US2013/054529 IPRP, Feb. 17, 2015.
WO, PCT/US2015/012293 ISR, Apr. 30, 2015.
WO, PCT/US2015/012096 ISR and Written Opinion, Jun. 29, 2015.
Olijhoek, J. K., et al., "The Metabolic Syndrome is associated with advanced vascular damage in patients with coronary heart disease, stroke, peripheral arterial disease or abdominal aortic aneurysm", European Heart Journal, 2004, vol. 25, No. 4, pp. 342-348.

(56) References Cited

OTHER PUBLICATIONS

Stoner, L., et al., "Relationship between blood velocity and conduit artery diameter and the effects of smoking on vascular responsiveness", J. Appl. Physiol., 2004, vol. 96, pp. 2139-2145.
WO, PCT/US2014/061256 ISR, Jan. 22, 2015.
U.S. Appl. No. 15/006,926 Non-Final Office Action, May 4, 2016.
U.S. Appl. No. 14/601,170 Non-Final Office Action, May 5, 2016.
WO, PCT/US2014/061256 IPRP, Apr. 19, 2016.
Hassan, S., et al., "Systolic time intervals: a review of the method in the non-invasive investigation of cardiac function in health, disease and clinical pharmacology", Postgraduate Medical Journal, 1983, vol. 59, pp. 423-434.
Heckman, J. L., et al., "Frequency analysis approach to the origin of the first and second heart sounds", American Heart Journal, 1982, vol. 104, pp. 1309-1318.
Wikipedia, Cardiac cycle, published Nov. 14, 2012.
U.S. Appl. No. 13/964,631 Office Action, Jan. 21, 2016.
Yokobori, Jr., A. T., et al., "The Analysis and Diagnosis of Unstable Behavior of the Blood Vessel Wall with an Aneurysm Based on Noise Science", Journal of Atherosclerosis and Thrombosis, 2006, vol. 13, No. 4, pp. 163-174.
EP, 13829710.6 Extended Search Report, Mar. 1, 2016.
Harada, A., et al., "Development of a Non-invasive Real-time Measurement System of Wave Intensity", IEEE Ultrasonics Symposium, 2000, pp. 1517-1520.
Khir, A. W., et al., "Wave intensity I the ascending aorta: effects of arterial occlusion", Journal of Biomechanics, 2005, vol. 38, pp. 647-655.
Sugawara, M., et al., "Clinical usefulness of wave intensity analysis", Med. Biol. Eng. Comput., 2009, vol. 47, pp. 197-206.
Swillens, A., et al., "Effect of an Abdominal Aortic Aneurysm on Wave Reflection in the Aorta", IEEE Transactions on Biomedical Engineering, 2008, vol. 55, No. 5, pp. 1602-1611.
Van Den Wijngaard, J. P.H.M., et al., "Comparison of arterial waves derived by classical wave separation and wave intensity analysis in a model of aortic coarctation", Med. Biol. Eng. Comput., 2009, vol. 47, pp. 211-220.

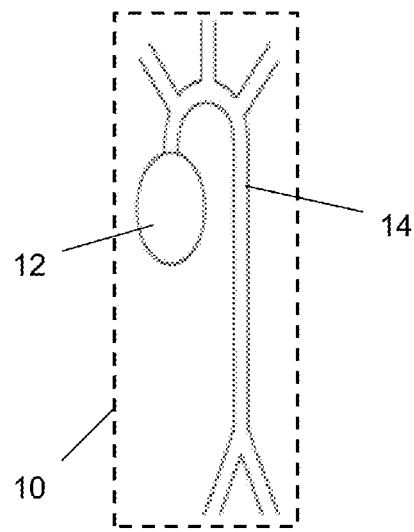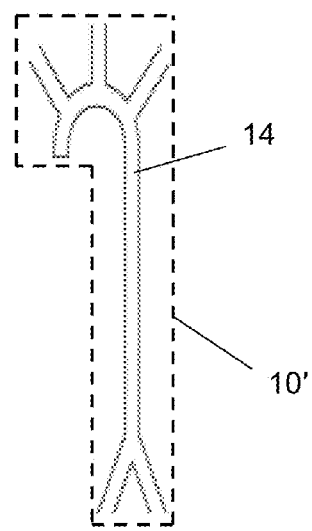
Fig. 1A  Fig. 1B
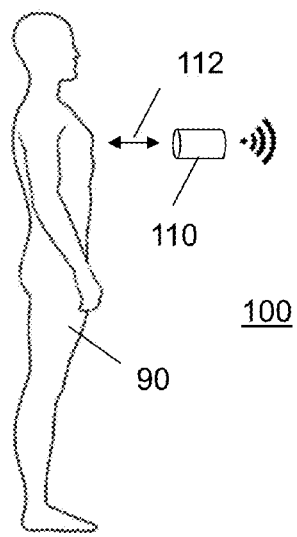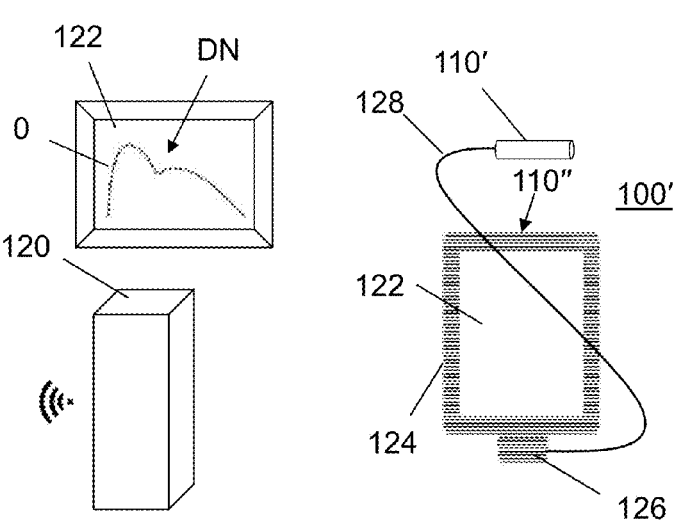
Fig. 2A  Fig. 2B

US 9,480,406 B2

INTRINSIC FREQUENCY ANALYSIS FOR LEFT VENTRICLE EJECTION FRACTION OR STROKE VOLUME DETERMINATION

RELATED APPLICATIONS

This filing claims the benefit of and priority to U.S. Provisional Patent Application Ser. Nos. 61/893,063, filed Oct. 18, 2013, and 62/003,735, filed May 28, 2014, both of which are incorporated by reference herein in their entirety and for all purposes.

FIELD

This filing relates to hemodynamic waveform analysis for left ventricle ejection fraction and/or stroke volume determination.

BACKGROUND

Cardiovascular diseases (CVDs) are the underlying cause of about one of every three deaths in United States each year. Likewise, about 34% of American adults are suffering from one or more types of CVD. In 2010, the total direct and indirect cost of CVDs was approximately $503 billion.

Certainly, there is an urgent need to develop new methods and devices for diagnosing and monitoring CVDs. Diagnosis enables early intervention and remediation. Monitoring may be a useful tool in behavior modification and prediction, as well as in the avoidance of an acute event leading to emergency hospitalization, morbidity and/or mortality. New methods and devices to meet these and other needs advantageously employ noninvasive measurement to reduce medical complications and increase patient comfort. Ideally, they are also easy to use by medical personnel and subjects themselves, especially in a home environment.

SUMMARY

Example embodiments of methods, systems, and devices based on Intrinsic Frequency (IF) concepts are described that enable measuring Left Ventricle Ejection Fraction (LVEF), Cardiac Output (CO), and Stroke Volume (SV) noninvasively. These embodiments consider the Intrinsic Frequencies associated with blood flow, in terms of its pressure wave, associated wall displacement wave, and/or flow wave, in order to perform the subject calculations. In many embodiments, only the shape of the waves, without magnitude, are used for such calculations. Noninvasive methods, systems and devices can also be used for measurements without the requirement for calibration.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE DRAWINGS

The figures provided herein may be diagrammatic and are not necessarily drawn to scale, with some components and features exaggerated and/or abstracted for clarity. Variations from the embodiments pictured are contemplated. Accordingly, depiction of aspects and elements in the figures are not intended to limit the scope of the claims, except when such intent is explicitly stated therein.

FIGS. 1A and 1B diagrammatically illustrate the dynamic coupling of the heart and aorta in a human circulatory system.

FIGS. 2A and 2B are perspective views depicting example embodiments of the IF processing system.

DETAILED DESCRIPTION

Figure 3:
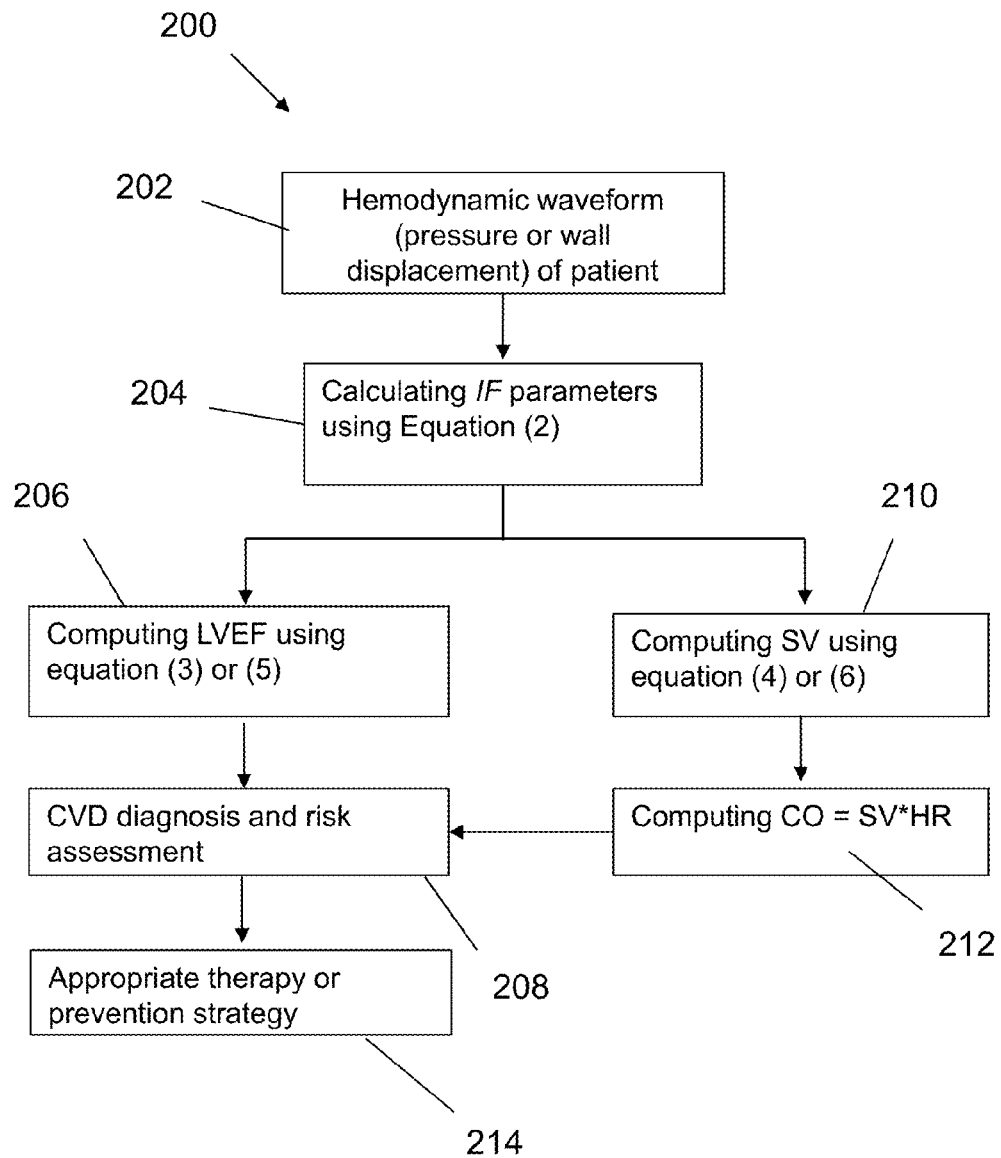
FIG. 3 is a flowchart depicting an example embodiment of a method of assessing IF parameters and performing a diagnosis.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is acknowledged that express recitation of every possible combination and substitution is overly burdensome, especially given that the permissibility of each and every such combination and substitution will be readily recognized by those of ordinary skill in the art.

As explained in USPPN 2013/0184573, pressure and flow waves generated by the heart propagate in the compliant arterial vasculature. FIG. 1A illustrates a coupled heart-aorta system 10 in systole, with the aortic valve open (not shown) and blood being pumped by the heart 12 into the aorta 14. As such, the heart and aorta construct a coupled dynamic system before the closure of the aortic valve. As shown in FIG. 1B, after the valve closure during diastole, the heart and aorta systems are decoupled in a second system state 10'.

The aortic waves in each state include information about heart dynamics, arterial network dynamic and heart-aorta coupling. Extraction of such information by analysis as described in further detail herein is based on Intrinsic Frequency (IF) methodology enabling the calculation or approximation of:

- Left Ventricle Ejection Fraction (LVEF) from an arterial pressure waveform alone;
- left ventricle Stroke Volume (SV) of the heart from such a pressure waveform alone;
- Cardiac Output (CO) of the heart from such a pressure waveform alone;
- Left Ventricle Ejection Fraction (LVEF) from an arterial wall displacement waveform alone;
- left ventricle Stroke Volume (SV) from such a wall displacement waveform alone; and/or
- Cardiac Output (CO) from such a wall displacement waveform alone.

Notably, traditional methods of data analysis are based on the assumption of that the data will be stationary and linear. Fourier analysis is just a typical, and often used, method. However, it is a known fact that the stationariness and linearity assumptions do not hold for arterial waves. Accordingly, a new method of Sparse Time-Frequency Representation (STFR) has been developed that may be applied herein to achieve the above, and still other methods and goals.

The STFR method is employed because it is well suited for nonlinear data analysis, it is less sensitive to noise perturbation and, it preserves some intrinsic physical property of the signal. The general STFR problem is defined as follows:

Minimize $M$

Subject to: $s(t)=\Sigma_{i=1}^{M} a_i(t)\cos \theta_i(t), a_i(t)\cos \theta_i(t) \oplus D$,
$(i=1, \ldots, M)$ (1)

In the embodiments described herein a simplified and modified version of STFR may be employed by minimizing.

$$\|f(t) - a_1 X(0, T_0)\cos\omega_1 t - b_1 X(0, T_0)\sin\omega_1 t - a_2 X(T_0, T)\cos\omega_2 t - b_2 X(T_0, T)\sin\omega_2 t - c\|_2^2 \quad (2)$$

$$X(a, b) = \begin{cases} 1 & a \leq t \leq b \\ 0 & \text{otherwise} \end{cases}$$

Subject to:

$$\begin{cases} a_1 \cos \omega_1 T_0 + b_1 \sin \omega_1 T_0 = a_2 \cos \omega_2 T_0 + b_2 \sin \omega_2 T_0 \\ a_1 = a_2 \cos \omega_2 T + b_2 \sin \omega_2 T \end{cases}$$

where, $T_0$ is the time of aortic valve closure (i.e., at a measured or charted Dicrotic Notch in a hemodynamic waveform) in order to determine IF $\omega_1$, $\omega_2$ values and other IF parameters such as $a_1$, $b_1$, $a_2$, $b_2$, and c constants fit to the waveform in the two domains on either side of the Dicrotic Notch. Further details regarding IF parameter determination are described in USPPN 20130184573, which is incorporated by reference in its entirety for all purposes.

LVEF and/or SV can be determined as shown in equations 3 and 4:

$$\text{LVEF} = f_1(\text{IFs}, p_{min}, p_{max}, p_{mean}, T_0, \text{HR}) \quad (3)$$

$$\text{SV} = f_2(\text{IFs}, p_{min}, p_{max}, p_{mean}, T_0, \text{HR}) \quad (4)$$

where IF s are the intrinsic frequency parameters ($\omega_1$, $\omega_2$, $a_1$, $b_1$, $a_2$, $b_2$, and c), $p_{min}$ is the minimum of the hemodynamic waveform signal (which, as will be understood by those of ordinary skill in the art, can be measured with a device that outputs a signal, for example, in terms of voltage, light intensity, microwave intensity, other wave intensity, displacement, or pressure) in the cardiac cycle corresponding to diastolic pressure, $p_{max}$ is the maximum of the signal (which again can be in terms of voltage, pressure, etc. per above) in the cardiac cycle corresponding to systolic pressure, $p_{mean}$ is the mean of the signal (again, in terms of voltage, pressure, etc.) over the whole cardiac cycle, $T_0$ is left ventricle ejection time or the notch time (i.e., time from the onset of the waveform to notch), and HR is the heart rate. Cardiac Output (CO) can be calculated by multiplying SV and HR.

The combination of parameters used in these formulas depends on the location where the waveform is measured and the nature of the waveform obtained (e.g., as between a pressure wave, vessel wall displacement wave and skin motion wave). As empirically determined, in the case of using ascending aortic pressure waveforms, $f_1$ and $f_2$ in equations 3 and 4 become expressions as in equation 5 and 6 below, respectively. As such, LVEF and/or SV can be calculated using the equations:

$$LVEF = k_1 - k_2\left(\frac{SR}{1-SR}\right)C_R\frac{\omega_1}{\omega_2} \quad (5)$$

$$SV = k_3\left(\omega_2 - k_4\left(\frac{SR}{1-SR}\right)C_R\omega_1\right) \quad (6)$$

where SR is the systolic time ratio (SR=$T_0$/HR) and $k_1$, $k_2$, $k_3$, and $k_4$ are universal constants. $C_R$ can be calculated using the following equation:

$$C_R = \frac{c - p_{min}}{p_{max} - p_{min}} \quad (7)$$

These waveforms employed can be acquired and/or processed using systems as illustrated in FIGS. 2A and 2B. Waveforms captured and/or IF results based on the same may be produced and/or displayed in real time for physician evaluation and/or logged for monitoring or subsequent evaluation of a physician or other analysis. Alternatively, diagnosis based on the IF results may be displayed, alarms may be triggered, and so forth, for users who are not either medically or specially trained (e.g., as in the case of home use or general practice physicians).

Regardless, what is meant by "real time" in the context above will generally mean that it takes about 1 second or less from the time of data acquisition for calculation and data presentation. Ideally, such action occurs or is performed without perceptible delay. However stated, real time activity in the subject embodiments concerns manipulation of such a mass of data and calculations that the task is well beyond practicable human capacity, thereby requiring the use of a computer processor.

In any case, FIG. 2A diagrammatically illustrates a computer-based system 100 in which a scanner 110 includes on-board electronics for sending and receiving signals 112 to acquire hemodynamic waveform measurements. Use of microwave sensor (at least for measuring vessel displacement) and/or ultrasound sensors (for measuring either or both of vessel distension and blood velocity/flow) for such purposes is well known. An example of suitable publicly-available hardware includes that employed in the GE LOGIQ Book Portable Ultrasound Machine, which technology is readily adapted to the subject methods and systems. Suitable microwave sensor technology is described in Fletcher, R R, and S Kulkarni, "Clip-on wireless wearable microwave sensor for ambulatory cardiac monitoring," IEEE, 2010. 365-369. Web. 3 Feb. 2012.

Other types of scanners may be used as well. These include tonomeric and optical units. In the former case, the tonomeric sensor will include a force or pressure sensing transducer producing an electronic signal (e.g., voltage output) corresponding to a pressure or wall-displacement based hemodynamic waveform. The optical scanner may embody any of a variety of technologies in producing a signal that correlates to a hemodynamic waveform. In one embodiment, the optical scanner may include infrared (IR) diode(s) and sensor(s) suitable for measuring a wall displacement waveform. In another embodiment, the scanner operates as a camera. In which case (whether in a flat-bed scanner format, in typical stand-alone digital camera format, or incorporated in the bezel of a iPAD or the like), such a device is able to capture a printed or otherwise displayed hemodynamic waveform and convert it to a digital representation employing a CCD, CMOS or the like. Then, a computer program such as the UN-SCAN-IT Graph Digitizer can be employed to produce a signal representative of the captured hemodynamic waveform to be received by a computer processor for analysis.

Accordingly, scanner 110 may be hand-held for scanning a seated or standing patient 90 as shown. Or the scanner hardware may be incorporated in a C-arm or tunnel for scanning a patient lying down. Other scanner hardware options are presented in U.S. Pat. Nos. 5,363,855 and 5,439,001, both of which are incorporated herein by reference in their entirety for all purposes, as well as the incorporated USPPN 20130184573 document.

A hand-held scanner may advantageously be battery-powered so as to avoid connection to a wall socket. Whether hand-held or incorporated or in a larger unit, scanner 110 may interface by wireless (as indicated) or wired (not shown) communication with a general purpose computer 120, optionally including display 122 to perform and communicate results, respectively. Otherwise, on-board processing and/or display hardware may be provided in connection with the sensor housing itself. Such options may be especially useful for a hand-held or semi-portable device as these may be used by a patient/subject at home, during travel, etc.

Notably, all the hardware may be located in one location. Alternatively, the computer system may be located at a remote location as in a "Cloud" based option. Further, the system may consist of the computer and its programming without a sensor means. In such a case, the system may include an optical scanner or other camera means for image or other electronic capture of a waveform produced by another (already available) measurement machine (e.g., the aforementioned GE scanner, etc.).

As yet another option, FIG. 2B, illustrates a portable system 100'. It includes a tablet-style computer device 124 (e.g., an iPAD) with an integral display 122. A tonomeric or optical scanner 110' is shown connected to computer 124 via a bus 126 and wired connection 128. However, the scanner (of whatever type) may be wirelessly connected as in the previous example as well. Alternatively, the scanner employed in capturing the hemodynamic waveform may be the camera 110" integrated in the device.

Regardless of how the hemodynamic waveform(s) is/are acquired, a given waveform can be analyzed as described in the embodiment of FIG. 3. Specifically, in method 200 one or more waveforms are obtained for analysis at 202. The data may originally be in digital form or converted thereto. It may come from a pressure wave, wall displacement wave and/or flow wave. However obtained, at 204, IF parameters can be calculated per Equation (2).

At 206, Left Ventricle Ejection Fraction (LVEF) may be calculated. From this, at 208, diagnosis may be made regarding cardiovascular disease (CVD) together with an assessment of associated risk. Doing so based on ejection fraction values is something within the common capabilities of physicians. Such diagnosis and/or assessment may instead by computerized. Likewise, assigning or recommending an appropriate therapy or prevention strategy may be offered at 214 by a physician or prompted by look-up and output from a computer database.

In addition to or as an alternative to LVEF calculation, the subject system may calculate Stroke Volume (SV) as at 210. Once obtained, cardiac output (CO) can be calculated at 212 as the product of SV and a subject's heart rate. Diagnosis/assessment (as at 208) may follow as may recommended therapy/prevention activity (as at 214).

Examples

Figures 4A, 4B:
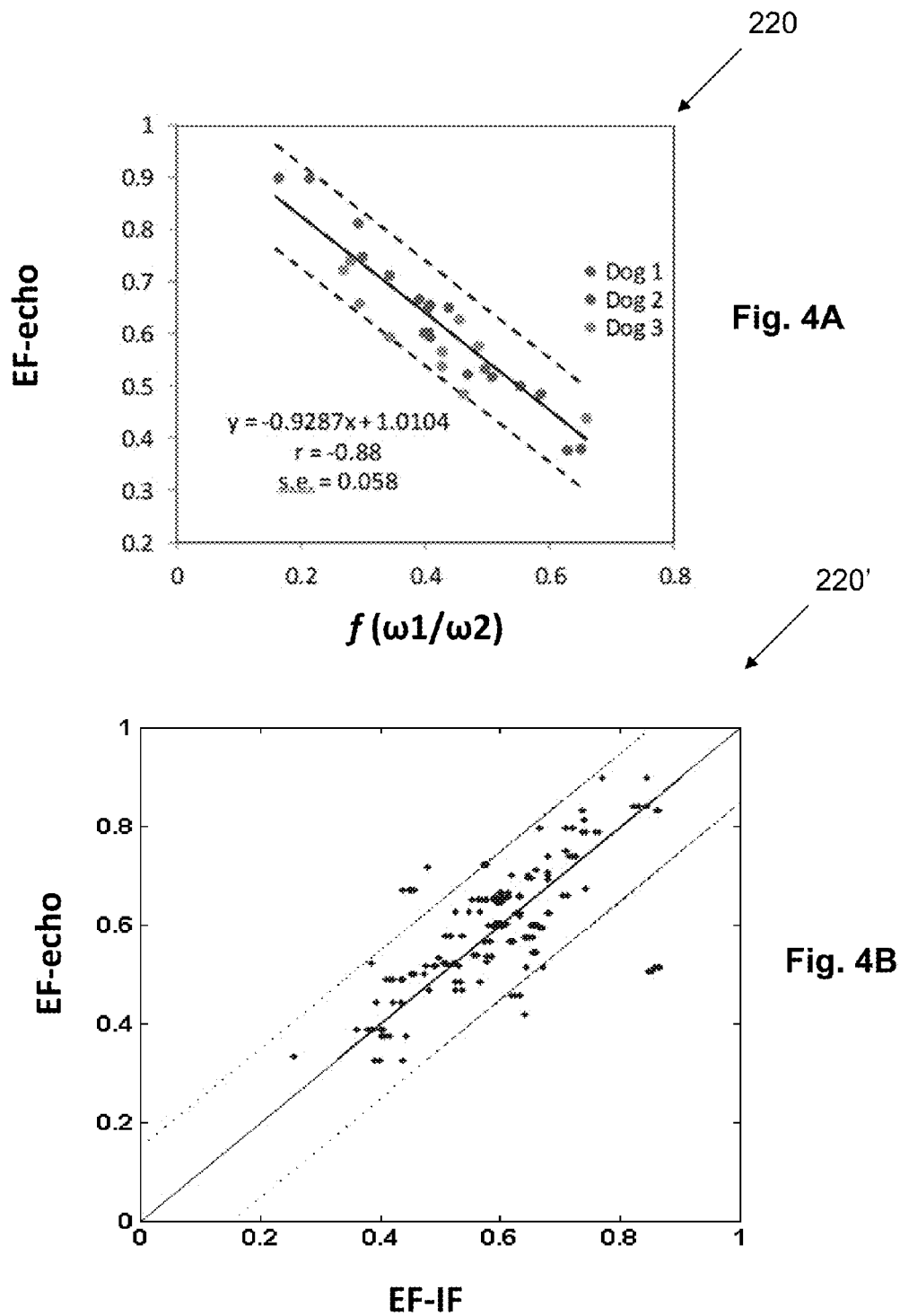
FIG. 4A is a chart correlating measured Ejection Fraction and Intrinsic Frequency parameters.
FIG. 4B is a chart correlating measured ejection fraction and Ejection Fraction calculated from Intrinsic Frequency.

FIG. 4A presents a chart 220 demonstrating the correlation between invasively measured and IF parameters ($\omega 1$ and $\omega 2$) calculated using equation (5). Here, pressure and echocardiogram data are from sampling with three dogs. Pressure was measured invasively and EF was measured by echocardiogram. In the chart, EF measured by 2D echocardiography methodology is presented (y-axis, EF-echo) versus the IF parameters calculated via equation 5 (x-axis, $f(\omega 1$ and $\omega 2)$ employing invasive ascending aortic pressure waveforms that were measured simultaneously with the 2D echo procedure. The two dashed lines are ±10% error lines. (Notably, EF-echo by itself inherently includes 15% error.) As such, chart 220 indicates excellent agreement between direct EF measurement and those derived by IF method in calculation of EF from waveform information.

In FIG. 4B, chart 220' illustrates a related comparison with six dogs. As above, IF methodology was employed using a modified version of Sparse Time-Frequency Representation (STFR) to extract the Intrinsic Frequencies ($\omega 1$ and $\omega 2$) from the pressure wave measured invasively in the dogs. As shown, LVEF calculated from IF is presented along the x-axis of the graph as compared to LVEF measured by standard echocardiography (EF-echo). Again, the results demonstrate a strong agreement between the EF-echo and the ejection fractions approximated from the IF parameters. The dotted lines represent ±15% error lines. Most importantly, all low ejection fraction data points (<40%) are within the error boundary.

Figure 5:
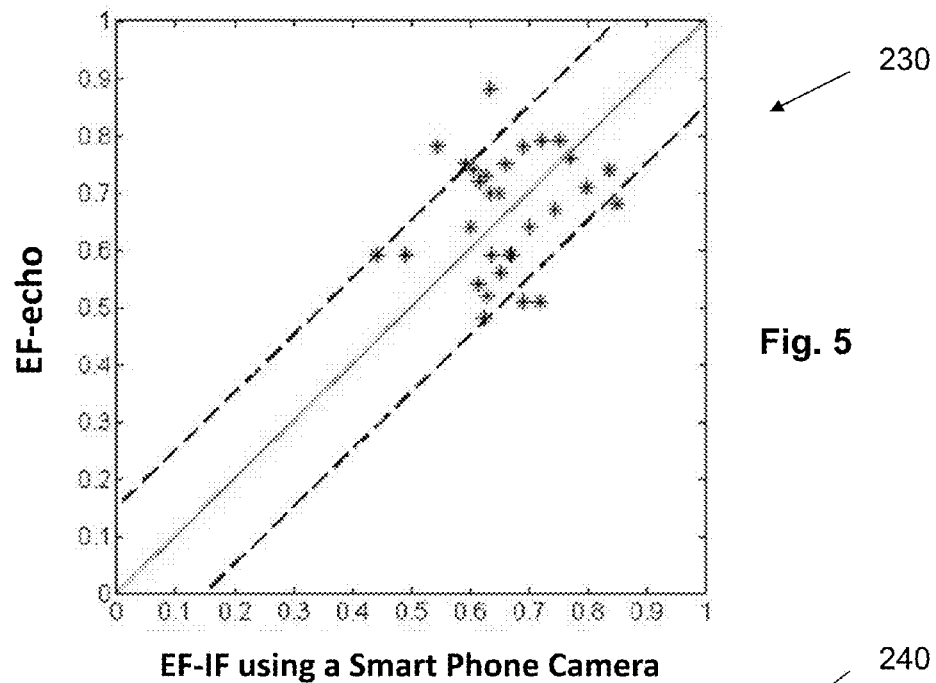
FIGS. 5 and 6 are charts comparing Ejection Fraction calculated with human subjects from the 2D echocardiography versus Ejection Fraction calculated with the subject IF methodology using skin motion waveform at a carotid artery location.

The intrinsic frequencies can also be extracted from measurement of the motion of the skin in locations where an artery is passing underneath the skin such as at the neck (carotid location), arm (brachial location) and wrist (radial location). In FIG. 5, chart 230 shows ejection fraction calculated from the 2D echocardiography (EF-echo) versus EF calculated from the IF method (EF-IF) using skin motion waveform at the neck (carotid artery location) of human test subjects. The skin motion waveforms were measured using a smart phone camera and light. Again, equation 5 was used to calculate EF with k1 and k2 both about equal to 1 offering optional solution. The dotted lines in the chart are 15% error lines. Again, excellent agreement between the echo- and IF-based is demonstrated. Other functions might be used in the alternative after further study.

Figure 6:
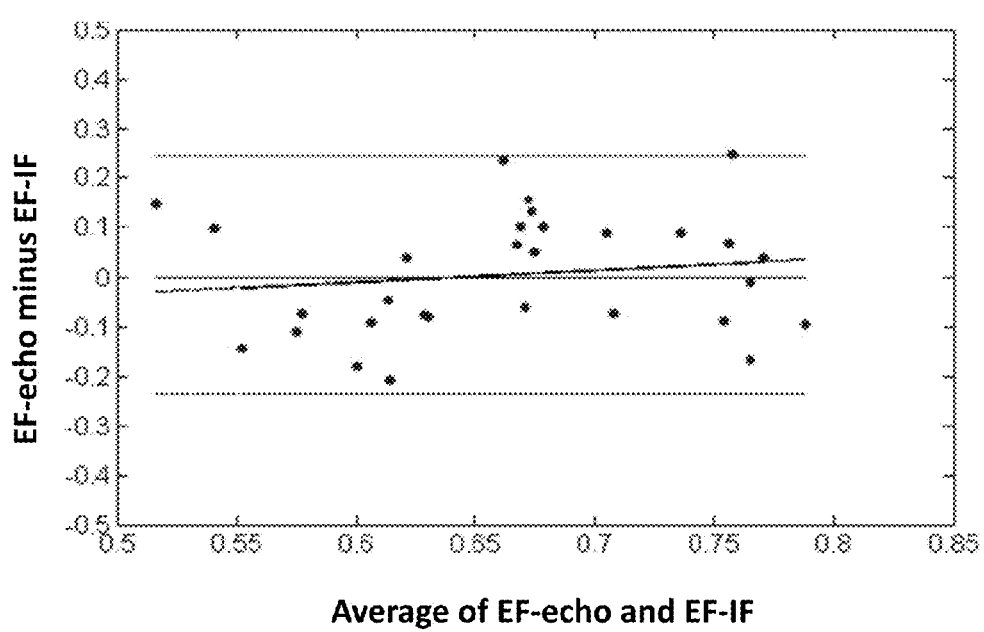

For the same measurements and calculations represented in FIG. 5, FIG. 6 provides a Bland Altman plot 240 showing the agreement between the clinically established EF-echo method and the subject EF-IF method from skin wave motion. As evident, there is no evidence of any particular proportional or magnitude related error. Rather, an overall systemic variability is noted that is consistent with the above-referenced error in echocardiography EF measurement.

Variations

In addition to the embodiments that been disclosed in detail above, still more are possible within the classes described and the inventors intend these to be encompassed within this Specification and claims. This disclosure is intended to be exemplary, and the claims are intended to cover any modification or alternative which might be predictable to a person having ordinary skill in the art.

Moreover, the various illustrative processes described in connection with the embodiments herein may be implemented or performed with a general purpose processor, a Digital Signal Processor (DSP), an Application Specific Integrated Circuit (ASIC), a Field Programmable Gate Array (FPGA) or other programmable logic device (PLD), discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has a user interface port that communicates with a user interface, and which receives commands entered by a user, has at least one memory (e.g., hard drive or other comparable storage, and random access memory) that stores electronic information including a program that operates under control of the processor and with communication via the user interface port, and a video output that produces its output via any kind of video output format, e.g., VGA, DVI, HDMI, DisplayPort, or any other form.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein. The camera may be a digital camera of any type including those using CMOS, CCD or other digital image capture technology.

The steps of a method or algorithm described in connection with the embodiments disclosed herein may be embodied directly in hardware, in a software module executed by a processor, or in a combination of the two. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary embodiments, the functions described may be implemented in hardware, software, firmware, or any combination thereof. If implemented in software, the functions may be stored on, transmitted over or resulting analysis/calculation data output as one or more instructions, code or other information on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

Operations as described herein can be carried out on or over a website. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

Also, the inventors intend that only those claims which use the words "means for" are intended to be interpreted under 35 USC 112, sixth paragraph. Moreover, no limitations from the specification are intended to be read into any claims, unless those limitations are expressly included in the claims. The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, it is contemplated that any optional feature of the embodiment variations described may be set forth and claimed independently, or in combination with any one or more of the features described herein. Reference to a singular item, includes the possibility that there is a plurality of the same items present. More specifically, as used herein and in the appended claims, the singular forms "a," "an," "said," and "the" include plural referents unless specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A system for acquiring and analyzing a hemodynamic waveform of a subject by Intrinsic Frequency (IF) analysis, the system comprising:
   a scanner adapted to capture a signal corresponding to a hemodynamic waveform; and
   at least one computer processor connected to the scanner by a wired or wireless connection, wherein the computer processor is adapted to receive the signal for the hemodynamic waveform, determine a Dicrotic Notch using the signal, calculate first and second intrinsic frequencies ($\omega_1$, $\omega_2$) on each side of the Dicrotic Notch and at least one of other IF parameters including $a_1$, $b_1$, $a_2$, $b_2$, and c for the waveform, and output a signal corresponding to at least one of left ventricle ejection fraction (LVEF) and stroke volume (SV).

2. The system of claim 1, wherein LVEF is calculated as a function of the IF parameters and $p_{min}$, $p_{max}$, $p_{mean}$, $T_0$ and HR.

3. The system of claim 1, wherein SV is calculated as a function of the IF parameters and $p_{min}$, $p_{max}$, $p_{mean}$, $T_0$ and HR.

4. A non-transitory computer readable medium having stored thereon instructions, which when executed cause one or more processors to:
   determine a Dicrotic Notch using an input signal corresponding to a hemodynamic waveform;
   calculate, by Intrinsic Frequency (IF) analysis, first and second intrinsic frequencies ($\omega_1$, $\omega_2$) on each side of the Dicrotic Notch and at least one of other IF parameters including $a_1$, $b_1$, $a_2$, $b_2$, c for the hemodynamic waveform; and
   output a signal corresponding to at least one of left ventricle ejection fraction (LVEF) and stroke volume (SV).

5. The computer readable medium of claim 4, including instructions for LVEF calculation as a function of the IF parameters and $p_{min}$, $p_{max}$, $p_{mean}$, $T_0$ and HR.

6. The computer readable medium of claim 4, including instructions for SV calculation as a function of the IF parameter and $p_{min}$, $p_{max}$, $p_{mean}$, $T_0$ and HR.

7. A method of analyzing a signal using a computer comprising a processor, the method comprising:
   noninvasively acquiring a signal for a hemodynamic waveform of a subject with a sensor device, wherein the signal is acquired without calibrating the sensor device, and wherein the sensor device outputs signal magnitude by a selection of voltage, light intensity, microwave intensity, displacement or pressure;
   analyzing, by the processor, the signal magnitude of each of a first section and a second section of the hemodynamic waveform signal, wherein the waveform includes a Dicrotic Notch, to determine first and second intrinsic frequencies ($\omega 1$, $\omega 2$) on opposite sides of the Dicrotic Notch; and
   outputting, by the processor, a result for at least one of left ventricle ejection fraction (LVEF) and stroke volume (SV).

8. The method of claim 7, wherein LFEF is calculated as a function of at least some of Intrinsic Frequency parameter ($\omega_1$, $\omega_2$, $a_1$, $b_1$, $a_2$, $b_2$, c) and $p_{min}$, $p_{max}$, $p_{mean}$, $T_0$ and HR.

9. The method of claim 7, wherein SV is calculated as a function of at least some of Intrinsic Frequency parameter ($\omega_1$, $\omega_2$, $a_1$, $b_1$, $a_2$, $b_2$, c) and $p_{min}$, $p_{max}$, $p_{mean}$, $T_0$ and HR.

10. The method of claim 7, wherein the waveform is selected from an arterial pressure wave, a wall displacement wave, a flow wave, or a velocity wave.

11. The method of claim 10, wherein the waveform is obtained from skin motion.

* * * * *